United States Patent
Naritomi et al.

(10) Patent No.: US 11,406,969 B2
(45) Date of Patent: Aug. 9, 2022

(54) METAL OXIDE CATALYST, METHOD FOR PRODUCING SAME, AND APPARATUS FOR PRODUCING SAME

(71) Applicant: ASAHI KASEI KABUSHIKI KAISHA, Tokyo (JP)

(72) Inventors: Miho Naritomi, Tokyo (JP); Kenji Akagishi, Tokyo (JP); Hiroyuki Yanagi, Tokyo (JP); Hiroyuki Yano, Tokyo (JP)

(73) Assignee: ASAHI KASEI KABUSHIKI KAISHA, Tokyo (JP)

(*) Notice: Subject to any disclaimer, the term of this patent is extended or adjusted under 35 U.S.C. 154(b) by 650 days.

(21) Appl. No.: 16/094,779

(22) PCT Filed: May 24, 2017

(86) PCT No.: PCT/JP2017/019336
§ 371 (c)(1),
(2) Date: Oct. 18, 2018

(87) PCT Pub. No.: WO2017/208926
PCT Pub. Date: Dec. 7, 2017

(65) Prior Publication Data
US 2019/0118166 A1 Apr. 25, 2019

(30) Foreign Application Priority Data
May 30, 2016 (JP) .............................. JP2016-107339

(51) Int. Cl.
*B01J 23/887* (2006.01)
*B01J 37/04* (2006.01)
(Continued)

(52) U.S. Cl.
CPC ............. *B01J 23/887* (2013.01); *B01J 37/04* (2013.01); *B01J 37/08* (2013.01); *C07B 61/00* (2013.01);
(Continued)

(58) Field of Classification Search
CPC .......... B01J 23/887; B01J 37/04; B01J 37/08; C07B 61/00; C07B 5/48; C07B 11/167
See application file for complete search history.

(56) References Cited

U.S. PATENT DOCUMENTS

| 2004/0147393 A1 | 7/2004 | Hibst et al. |
| 2014/0171303 A1 | 6/2014 | Yoshida et al. |
| 2014/0200380 A1* | 7/2014 | Josch .................... C07C 7/08 585/621 |

FOREIGN PATENT DOCUMENTS

| DE | 10 2010 021 792 A1 | 12/2011 |
| EP | 3 023 148 A1 | 5/2016 |

(Continued)

OTHER PUBLICATIONS

English translation of Written Opinion of the International Searching Authority dated Aug. 22, 2017, in PCT/JP2017/019336.
(Continued)

*Primary Examiner* — James A Fiorito
(74) *Attorney, Agent, or Firm* — Birch, Stewart, Kolasch & Birch, LLP

(57) ABSTRACT

A metal oxide catalyst, which has a bulk composition represented by formula (1) below and which is used to produce a conjugated diolefin by an oxidative dehydrogenation reaction between a monoolefin, having 4 or more carbon atoms, and molecular oxygen, wherein standard deviation obtained by dividing a ratio of Bi molar concentration relative to Mo molar concentration at the surface of a catalyst particle by a ratio of the Bi molar concentration relative to the Mo molar concentration in a catalyst bulk is 0.3 or less.

$$Mo_{12}Bi_pFe_qA_aB_bC_cD_dE_eF_fO_x \qquad (1)$$

(In the formula, A is at least one type of element selected from the group consisting of Ni and Co, B is at least one type of element selected from among alkali metal elements, C is at least one type of element selected from the group consisting of Mg, Ca, Sr, Ba, Zn and Mn, D is at least one type of rare earth element, E is at least one type of element selected from the group consisting of Cr, In and Ga, F is at least one type of element selected from the group consisting of Si, Al, Ti and Zr, O is oxygen, p, q, a, b, c, d, e, f and x denote the number of atoms of Bi, Fe, A, B, C, D, E, F and oxygen, respectively, relative to 12 Mo atoms, and are such that $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, (Continued)

$0 \leq e \leq 5$ and $0 \leq f \leq 200$, and x is the number of oxygen atoms required to satisfy valency requirement of other elements present.)

6 Claims, 2 Drawing Sheets

(51) Int. Cl.
*C07C 5/48* (2006.01)
*C07C 11/167* (2006.01)
*C07B 61/00* (2006.01)
*B01J 37/08* (2006.01)
*B01F 25/42* (2022.01)

(52) U.S. Cl.
CPC .............. *C07C 5/48* (2013.01); *C07C 11/167* (2013.01); *B01F 25/42* (2022.01); *B01J 2523/54* (2013.01); *B01J 2523/68* (2013.01); *B01J 2523/842* (2013.01); *C07C 2523/887* (2013.01)

(56) References Cited

FOREIGN PATENT DOCUMENTS

| | | |
|---|---|---|
| JP | 4-182450 A | 6/1992 |
| JP | 2004-231509 A | 8/2004 |
| JP | 2010-120933 A | 6/2010 |
| JP | 2013-146655 A | 8/2013 |
| JP | 5371692 B2 | 12/2013 |
| JP | 2017-056398 A | 3/2017 |
| WO | WO 2013/002029 A1 | 1/2013 |

OTHER PUBLICATIONS

International Search Report for PCT/JP2017/019336 (PCT/ISA/210) dated Aug. 22, 2017, with English translation.
Written Opinion of the International Searching Authority for PCT/JP2017/019336 (PCT/ISA/237) dated Aug. 22, 2017.
"Basic Organic Synthesis Translation Series Eighth," Basic organic synthesis translation group compilation, published by Shanghai Science and Technology Compiler, Mar. 31, 1996, pp. 12-17 (9 pages total).
English translation of Chinese Office Action of the corresponding Chinese Patent Application No. 201780033218.9 dated Jul. 20, 2021.

* cited by examiner

METAL OXIDE CATALYST, METHOD FOR PRODUCING SAME, AND APPARATUS FOR PRODUCING SAME

TECHNICAL FIELD

The present invention relates to a metal oxide catalyst, a method for producing same, and an apparatus for producing same.

BACKGROUND ART

Methods for producing 1,3-butadiene (hereinafter also referred to simply as "butadiene") by means of oxidative dehydrogenation reactions between n-butene and oxygen are well known.

For example, Patent Document 1 discloses a method for producing butadiene by filling a tablet-molded molybdenum-containing catalyst in a fixed bed reactor and supplying a raw material gas containing n-butene and oxygen to the reactor.

In addition, Patent Document 2 discloses a method for producing butadiene by filling a fluidized bed reactor with catalyst powder particles obtained by supporting an oxide of a metal such as Mo, Bi or Fe on a carrier such as silica, and then bringing the particles into contact with a raw material gas containing n-butene and oxygen.

The fixed bed reaction system disclosed in Patent Document 1 has the advantage of being able to increase the reaction yield because the gas flow state is close to extrusion flow, and is a reaction system that is also widely used in industry. However, fixed bed reaction systems have problems such as low heat conduction and being unsuitable for exothermic reactions and endothermic reactions that require heat removal or heating. In particular, in reactions that generate large amounts of heat, such as oxidative dehydrogenation reactions of n-butene, the temperature rises significantly and is difficult to control, and there are concerns regarding runaway reactions. Furthermore, this type of rapid temperature rise leads to problems such as catalysts being damaged and rapidly degraded.

However, because catalyst particles flow to a great extent in the reactor, the fluidized bed reaction system disclosed in Patent Document 2 achieves the advantageous effects of (1) exhibiting high heat conduction, being able to maintain the temperature inside the reactor almost uniformly even in the case of significantly exothermic or endothermic reactions, and being able to suppress excessive progress of a reaction, and (2) suppressing localized accumulation of energy, thereby enabling raw material gases to reaction within explosion limits and enabling an increase in raw material concentration and an improvement in productivity. Therefore, it can be said that fluidized bed reaction systems are suitable for oxidative dehydrogenation reactions of n-butene, which are highly exothermic reactions.

CITATION LIST

Patent Document

Patent Document 1: Patent Publication JP-A-2013-146655
Patent Document 2: Japanese Patent No. 5371692

SUMMARY

Technical Problem

Here, many Mo—Bi-containing metal oxide catalysts are known as catalysts used when producing conjugated diolefins such as butadiene from monoolefins such as n-butene, but it cannot be said that the performance of these catalysts is satisfactory.

Furthermore, there are problems in the prior art for this type of production method also. For example, the invention disclosed in Patent Document 1 requires an extremely complex process, namely first preparing a catalyst precursor, drying, firing, then pulverizing, and then preparing a catalyst again. In addition, Patent Document 2 also discloses a method for producing a catalyst, but a catalyst having sufficiently high catalyst performance cannot be obtained using this method.

Therefore, the purpose of the present invention is to provide a Mo—Bi-containing metal oxide catalyst which is used to produce a conjugated diolefin from a monoolefin and which achieves higher catalyst performance, and a method and apparatus for producing such a catalyst.

Solution to Problem

As a result of diligent research carried out in order to solve the problems mentioned above, the inventors of the present invention established that conventional Mo—Bi-containing metal oxide catalysts were non-uniform in terms of compositional ratio of Mo and Bi at the catalyst surface, and that satisfactory catalyst performance could not therefore be exhibited.

Furthermore, the inventors of the present invention found that Mo—Bi-containing metal oxide catalysts are generally produced using a slurry-like Mo—Bi-containing liquid obtained by mixing a Mo-containing liquid and a Bi-containing liquid, and that the method for mixing the Mo-containing liquid and the Bi-containing liquid greatly affects the uniformity of the compositional ratio of Mo and Bi at the catalyst surface. In addition, the inventors of the present invention found that by mixing a Mo-containing liquid and a Bi-containing liquid using a specific method when preparing the slurry, it is possible to produce a Mo—Bi-containing metal oxide catalyst having a uniform compositional ratio of Mo and Bi at the catalyst surface, and thereby completed the present invention.

That is, the present invention is as follows.

[1] A metal oxide catalyst, which has a bulk composition represented by formula (1) below and which is used to produce a conjugated diolefin by an oxidative dehydrogenation reaction between a monoolefin, having 4 or more carbon atoms, and molecular oxygen, wherein standard deviation obtained by dividing a ratio of Bi molar concentration relative to Mo molar concentration at the surface of a catalyst particle by a ratio of the Bi molar concentration relative to the Mo molar concentration in a catalyst bulk is 0.3 or less:

$$Mo_{12}Bi_pFe_qA_aB_bC_cD_dE_eF_fO_x \qquad (1)$$

(In the formula, A is at least one type of element selected from the group consisting of Ni and Co, B is at least one type of element selected from among alkali metal elements, C is at least one type of element selected from the group consisting of Mg, Ca, Sr, Ba, Zn and Mn, D is at least one type of rare earth element, E is at least one type of element selected from the group consisting of Cr, In and Ga, F is at least one type of element selected from the group consisting of Si, Al, Ti and Zr, O is oxygen, p, q, a, b, c, d, e, f and x denote the number of atoms of Bi, Fe, A, B, C, D, E, F and oxygen, respectively, relative to 12 Mo atoms, and are such that $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, $0 \leq e \leq 5$ and $0 \leq f \leq 200$, and x is the number of oxygen atoms required to satisfy valency requirement of other elements present.)

[2] The metal oxide catalyst according to [1], wherein the standard deviation is 0.2 or less and p in formula (1) is such that $0.15 \leq p \leq 3$.

[3] The metal oxide catalyst according to [1] or [2], wherein the monoolefin is n-butene.

[4] The metal oxide catalyst according to any one of [1] to [3], wherein the conjugated diolefin is 1,3-butadiene.

[5] The metal oxide catalyst according to any one of [1] to [4], wherein the oxidative dehydrogenation reaction is carried out as a fluidized bed reaction.

[6] A method for producing a metal oxide catalyst which has a bulk composition represented by formula (1) and which is used to produce a conjugated diolefin by an oxidative dehydrogenation reaction between a monoolefin, having 4 or more carbon atoms, and molecular oxygen, the method including:

(i) a strep of preparing a Mo-containing liquid that contains at least Mo and a Bi-containing liquid that contains at least Bi, (ii) a step of continuously supplying the Mo-containing liquid to a first flow path, continuously supplying the Bi-containing liquid to a second flow path, and merging the first flow path and the second flow path at a point further downstream than the positions, where the Mo-containing liquid and the Bi-containing liquid are supplied respectively, thereby mixing the Mo-containing liquid and the Bi-containing liquid and obtaining a Mo—Bi-containing liquid, and (iii) a step of drying the Mo—Bi-containing liquid:

$$Mo_{12}Bi_pFe_qA_aB_bC_cD_dE_eF_fO_x \quad (1)$$

(In the formula, A is at least one type of element selected from the group consisting of Ni and Co, B is at least one type of element selected from among alkali metal elements, C is at least one type of element selected from the group consisting of Mg, Ca, Sr, Ba, Zn and Mn, D is at least one type of rare earth element, E is at least one type of element selected from the group consisting of Cr, In and Ga, F is at least one type of element selected from the group consisting of Si, Al, Ti and Zr, O is oxygen, p, q, a, b, c, d, e, f and x denote the number of atoms of Bi, Fe, A, B, C, D, E, F and oxygen, respectively, relative to 12 Mo atoms, and are such that $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, $0 \leq e \leq 5$ and $0 \leq f \leq 200$, and x is the number of oxygen atoms required to satisfy valency requirement of other elements present.)

[7] The method for producing a metal oxide catalyst according to [6], further including the step of:

(iv) further mixing the Mo—Bi-containing liquid between the step (ii) and the step (iii).

[8] The method for producing a metal oxide catalyst according to [6] or [7], further including the step of:

(v) storing the Mo—Bi-containing liquid between the step (ii) and the step (iii).

[9] The method for producing a metal oxide catalyst according to [8], wherein a treatment including in series the steps (i), (ii) and (v) is carried out using a batch type treatment system, the entire amount of a batch of the Mo—Bi-containing liquid obtained in the the step (ii) is stored in the step (v), and in the step (ii), when the mass supply rates of the Mo-containing liquid and the Bi-containing liquid to the first flow path and the second flow path are denoted by mA (g/min) and mB (g/min) respectively, at least 60 mass % of the total supplied amounts MA (g) and MB (g) per batch of the Mo-containing liquid and the Bi-containing liquid are supplied in such a way as to satisfy formula (3):

$$(mB/mA)/(MB/MA)=0.5 \text{ to } 1.5 \quad (3).$$

[10] The method for producing a metal oxide catalyst according to [6] or [7], wherein the Mo—Bi-containing liquid is continuously supplied for the step (iii).

[11] The method for producing a metal oxide catalyst according to [6], [7] or [10], wherein in the step (ii), when molar supply rates of the Mo-containing liquid and the Bi-containing liquid to the first flow path and the second flow path are denoted by mα (mol/min) and mβ (mol/min) respectively, the Mo-containing liquid and Bi-containing liquid are supplied in such a way as to satisfy formula (4):

$$(m\beta/m\alpha)/(p/12)=0.8 \text{ to } 1.2 \quad (4).$$

[12] An apparatus for producing a metal oxide catalyst which has a bulk composition represented by formula (1) and which is used to produce a conjugated diolefin by an oxidative dehydrogenation reaction between a monoolefin having 4 or more carbon atoms and molecular oxygen, the apparatus including:

a first flow path for supplying a Mo-containing liquid that contains at least Mo, a second flow path for supplying a Bi-containing liquid that contains at least Bi, and a merging part where the first flow path and the second flow path merge:

$$Mo_{12}Bi_pFe_qA_aB_bC_cD_dE_eF_fO_x \quad (1)$$

(In the formula, A is at least one type of element selected from the group consisting of Ni and Co, B is at least one type of element selected from among alkali metal elements, C is at least one type of element selected from the group consisting of Mg, Ca, Sr, Ba, Zn and Mn, D is at least one type of rare earth element, E is at least one type of element selected from the group consisting of Cr, In and Ga, F is at least one type of element selected from the group consisting of Si, Al, Ti and Zr, O is oxygen, p, q, a, b, c, d, e, f and x denote the number of atoms of Bi, Fe, A, B, C, D, E, F and oxygen, respectively, relative to 12 Mo atoms, and are such that $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, $0 \leq e \leq 5$ and $0 \leq f \leq 200$, and x is the number of oxygen atoms required to satisfy valency requirement of other elements present.)

[13] The apparatus for producing a metal oxide catalyst according to [12], which also has a mixing device positioned downstream of the merging part.

[14] The apparatus for producing a metal oxide catalyst according to [12] or [13], wherein the mixing device is a static mixing device.

Advantageous Effects of Invention

According to the present invention, it is possible to provide a Mo—Bi-containing metal oxide catalyst having excellent catalyst performance, and also possible to provide a method and apparatus for continuously and stably producing such a catalyst.

DESCRIPTION OF EMBODIMENTS

A detailed explanation will now be given of a mode for carrying out the present invention (hereinafter referred to simply as "the present embodiment"). The present invention is not limited to the present embodiment given below, and can be variously altered within the gist of the invention.

<Mo—Bi-Containing Metal Oxide Catalyst>

The metal oxide catalyst of the present embodiment (hereinafter also referred to simply as "the catalyst") facilitates an oxidative dehydrogenation reaction that produces a conjugated diolefin from a monoolefin having 4 or more carbon atoms and molecular oxygen, and the bulk composition of this catalyst, that is, the proportions of elements that constitute the catalyst as a whole, is represented by formula (1) below.

Whether or not the bulk composition of a certain Mo—Bi-containing metal oxide catalyst satisfies the composition of formula (1) can be determined using a well-known quantitative element analysis method, for example, an ICP emission spectroscopic analysis method, an atomic absorption spectroscopy method, an ICP mass spectrometry method or a fluorescence X-Ray analysis method. The present working examples adopt compositions determined by an ICP emission spectroscopic analysis method.

$$Mo_{12}Bi_pFe_qA_aB_bC_cD_dE_eF_fO_x \quad (1)$$

(In the formula, A is at least one type of element selected from the group consisting of Ni and Co, B is at least one type of element selected from among alkali metal elements, C is at least one type of element selected from the group consisting of Mg, Ca, Sr, Ba, Zn and Mn, D is at least one type of rare earth element, E is at least one type of element selected from the group consisting of Cr, In and Ga, F is at least one type of element selected from the group consisting of Si, Al, Ti and Zr, O is oxygen, p, q, a, b, c, d, e, f and x denote the atomic ratios of Bi, Fe, A, B, C, D, E, F and oxygen, respectively, relative to 12 Mo atoms, and are such that $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, $0 \leq e \leq 5$ and $0 \leq f \leq 200$, and x is the number of oxygen atoms required to satisfy the valency requirement of the other elements present.)

By using a metal oxide catalyst having the bulk composition represented by formula (1), it is possible to produce a conjugated diolefin at a high yield.

It is preferable for A in formula (1) to be Ni or Ni and Co, B to be at least one element selected from the group consisting of K, Rb and Cs, C to be Mg, D to be Ce, E to be Cr, and F to be Si. In addition, the composition of formula (1) above is preferably such that $0.15 \leq p \leq 3$, $1.5 \leq q \leq 3.5$, $1.7 \leq a \leq 9$, $0.02 \leq b \leq 1$, $0.5 \leq c \leq 4.5$, $0.02 \leq d \leq 1.0$, $0 \leq e \leq 4.5$, and $10 \leq f \leq 100$.

If the constituent elements are those mentioned above and the atomic ratios of these elements fall within the ranges mentioned above, it is possible to produce butadiene at a significantly higher yield.

In particular, a case where F is Si and the value of f is such that $20 \leq f \leq 100$ is more preferred due to exhibiting suitable butadiene production reaction activity. By exhibiting suitable activity, it is possible to prevent localized heat accumulation caused by heat generated in the reaction, and possible to extend the life of the catalyst. It is further preferable for the value of f to be such that $20 \leq f \leq 50$.

In the present embodiment, a metal oxide catalyst having the bulk composition represented by formula (1) is such that the standard deviation obtained by dividing the ratio of the Bi molar concentration relative to the Mo molar concentration at the surface of a catalyst particle by the ratio of the Bi molar concentration relative to the Mo molar concentration in the catalyst bulk is 0.3 or less.

Here, the Mo molar concentration and the Bi molar concentration at the surface of catalyst particles can be determined by SEM-EDX (Scanning Electron Microscopes-Energy Dispersive X-Ray Spectroscopy) compositional analysis, and the Mo molar concentration and the Bi molar concentration in the catalyst bulk can be determined by, for example, an ICP emission spectroscopic analysis method.

In addition, the standard deviation can be determined using formula (2) below.

$$\text{Standard deviation} = \{((S_1-\mu)^2+(S_2-\mu)^2+\ldots+(S_{100}-\mu)^2)/100[\text{number}]\}^{1/2} \quad (2)$$

In formula (2), $S_k$ (k=1 to 100) is a value obtained by dividing, by $(Bi/Mo)_{bulk}$, the ratio $(Bi/Mo)_{surf}$, which is the Bi molar concentration relative to the Mo molar concentration at the surface of the $k^{th}$ catalyst particle among 100 arbitrarily selected catalyst particles. $(Bi/Mo)_{bulk}$ is the ratio of the Bi molar concentration relative to the Mo molar concentration in the catalyst bulk, as determined by an ICP emission spectroscopic analysis method. $\mu$ is the average value of 100 $S_k$ (k=1 to 100) (=$(S_1+S_2 \ldots +S_{100})/100$).

Standard deviation is an indicator of variation. A smaller standard deviation means less variation from the average value. Therefore, a lower value in formula (2) means that the surface composition of catalyst particles is more uniform.

According to the present invention, by using a catalyst in which the value of formula (2) is 0.3 or less when producing a conjugated diolefin by an oxidative dehydrogenation reaction between a monoolefin, having 4 or more carbon atoms, and molecular oxygen, the conjugated diolefin can be produced at a high yield. The value of formula (2) is preferably 0.2 or lower, more preferably 0.15 or lower, and further preferably 0.1 or lower.

<Method for Producing Metal Oxide Catalyst>

The above-mentioned metal oxide catalyst which has a uniform surface composition and which has a bulk composition represented by formula (1) can be produced by means of, for example, the production method of the present embodiment (hereinafter also referred to as "the first production method").

The first production method comprises the steps of: (i) preparing a Mo-containing liquid that contains at least Mo and a Bi-containing liquid that contains at least Bi, and (ii) mixing the Mo-containing liquid and the Bi-containing liquid so as to obtain a Mo—Bi-containing liquid, and further includes (iii) drying the Mo—Bi-containing liquid. The first production method may also include a firing step after step (iii).

Furthermore, in the first production method, it is possible to provide a step of further mixing the Mo—Bi-containing liquid (step (iv)) after mixing the Mo-containing liquid and the Bi-containing liquid to produce the Mo—Bi-containing liquid (slurry) and before the step of drying the Mo—Bi-containing liquid (that is, between step (ii) and step (iii)).

In addition, it is possible to provide a step of storing a certain amount of the Mo—Bi-containing liquid (step (v)) between step (ii) and step (iii).

The Mo—Bi-containing liquid prepared in step (ii) may be continuously supplied as-is to step (iii) or supplied for step (iii) after being subjected to step (iv), and some or all of the Mo—Bi-containing liquid may be temporarily stored (step (v)) and then supplied for (iii).

In cases where step (v) is provided and the Mo—Bi-containing liquid is temporarily stored, it is preferable to store all of the Mo—Bi-containing liquid prepared in step (ii) or store all of the Mo—Bi-containing liquid prepared by carrying out step (ii) and then step (iv) (a batch processing system). In the case of a batch processing system, even if a difference occurs in the supply ratio of the Mo-containing liquid and the Bi-containing liquid in step (ii), the entire amount of raw materials are mixed in step (v), that is, it is possible to supply the Mo—Bi-containing liquid to step (iii) after being unified to the desired catalyst composition.

In the present embodiment, it is possible to select either a continuous supply system or a batch processing system, but it is preferable to select a continuous supply system in cases where a catalyst is to be produced in a short time and to select a batch processing system in cases where the allowable difference in supply ratio is to be extended.

A detailed explanation will now be given as the first production method.

Step (i) and step (ii) are steps for preparing a slurry that contains catalyst raw materials.

Specifically, the first production method comprises the steps of: (i) preparing a Mo-containing liquid that contains at least Mo (a liquid that contains a raw material for Mo that serves as a catalyst component, hereinafter also referred to as "Liquid A") and a Bi-containing liquid that contains at least Bi (a liquid that contains a raw material for Bi that serves as a catalyst component, hereinafter also referred to as "Liquid B"), and (ii) mixing these liquids (hereinafter, the Mo-containing liquid and the Bi-containing liquid are also referred to as "the two liquids"). Mixing the two liquids forms a slurry that is a Mo—Bi-containing liquid.

This Mo—Bi-containing liquid is a precursor of the Mo—Bi-containing metal oxide catalyst, and through research, the inventors of the present invention better understood that conditions for producing this precursor greatly affect the uniformity of composition at the surface of produced catalyst particles.

In step (ii) in the present embodiment, the Mo-containing liquid and the Bi-containing liquid are continuously supplied to the first and second flow paths, respectively, and the first flow path and second flow path are merged at a position downstream from the positions, where the Mo-containing liquid and Bi-containing liquid are supplied respectively, thereby preparing the Mo—Bi-containing liquid and enabling production of catalyst particles having high surface composition uniformity.

Explanations will now be given of the raw materials of the elements that constitute the catalyst of the present embodiment.

Mo raw materials are preferably salts that are soluble in water, nitric acid, or the like, and an example thereof is ammonium molybdate, which is an ammonium salt.

Raw materials for Bi, Fe, Ni, Co, alkali metals (Li, Na, K, Rb, Cs and Fr), Mg, Ca, Sr, Ba, Zn, Mn, rare earth elements (Sc, Y, La, Ce, Pr, Nd, Pm, Sm, Eu, Gd, Tb, Dy, Ho, Er, Tm, Yb and Lu), Cr, In and Ga are also preferably salts that are soluble in water, nitric acid, or the like, and examples thereof include nitrates, hydrochlorides, sulfates and organic acid salts. Nitrates are particularly preferred from the perspective of ease of dissolution in water, nitric acid, or the like. Examples thereof include bismuth nitrate, iron nitrate, nickel nitrate, cobalt nitrate, potassium nitrate, rubidium nitrate, magnesium nitrate, calcium nitrate, strontium nitrate, barium nitrate, zinc nitrate, manganese nitrate, lanthanum nitrate, cerium nitrate, chromium nitrate, indium nitrate and gallium nitrate. It is possible to use one of these in isolation, or a combination of two or more types thereof.

Raw materials for Si, Al, Ti and Zr are preferably oxides such as $SiO_2$, $Al_2O_3$, $TiO_2$ and $ZrO_2$. $SiO_2$ is particularly preferred from the perspective of having few acid centers, which increase the amount of by-products generated in reactions for producing butadiene. Examples of $SiO_2$ raw materials include silica sols (also known as colloidal silica) and powdered silica. Silica sols are particularly preferred from the perspective of ease of handling. Examples thereof include Snowtex (available from Nissan Chemical Industries, Ltd.) and Nalco silica sol (available from Nalco Japan). In the case of a silica sol, the average particle diameter of the $SiO_2$ preferably falls within the range 5 to 100 nm, and more preferably falls within the range 10 to 50 nm. In addition, it is possible to use a mixture of silica sols having different average particle diameters.

Moreover, with the exception of oxygen atoms, the atomic ratios of the elements in the ultimately produced catalyst do not significantly differ from the atomic ratios in the catalyst raw materials used when producing the catalyst.

From the perspective of increasing the dispersibility of the catalyst raw material metals in the Mo-containing liquid, the Bi-containing liquid and the Mo—Bi-containing liquid, which is obtained by mixing these liquids, it is preferable to add an organic acid that can form a chelate with a metal element to the Mo-containing liquid, the Bi-containing liquid or the Mo—Bi-containing liquid, in addition to the catalyst raw materials mentioned above. The organic acid is not particularly limited, but preferred examples thereof include oxalic acid, tartaric acid, citric acid and malic acid, and the organic acid may be added to the Mo-containing liquid or the Bi-containing liquid, or to both of these liquids. In addition, a preferred mode is one in which the organic acid is added to a raw material for Si, Al, Ti or Zr, such as a silica sol. The organic acid can be added as a powder, a solid or an aqueous solution.

In addition, it is preferable to add an inorganic acid such as nitric acid, hydrochloric acid or sulfuric acid in order to increase the solubility of the metal salts that are catalyst raw materials. Nitric acid is particularly preferred from the perspective of volatilizing in the firing step described below and leaving little residue.

Furthermore, it is also preferable to add aqueous ammonia in order to increase the solubility of Mo in the Mo-containing liquid.

In the first production method, the Mo-containing liquid and the Bi-containing liquid are first prepared (step (i)).

It is preferable to prepare the Mo-containing liquid by dissolving or dispersing the Mo raw material in an aqueous medium such as water. It is also preferable to add aqueous ammonia to this liquid so as to increase the solubility of the Mo raw material. The concentration of Mo atoms in the Mo-containing liquid preferably falls within the range 0.1 to 30 wt %.

The Bi-containing liquid is prepared separately from the Mo-containing liquid. It is preferable to prepare the Bi-containing liquid by dissolving or dispersing the Bi raw material in an aqueous medium such as water. The Bi-containing liquid is preferably acidic, and it is preferable for the Bi-containing liquid to contain nitric acid in order to increase the solubility of the Bi raw material. The concentration of Bi atoms in the Bi-containing liquid preferably falls within the range 0.1 to 10 wt %.

Raw materials other than the Mo raw material and the Bi raw material, that is, raw materials for Fe, Ni, Co, alkali metals, Mg, Ca, Sr, Ba, Zn, Mn, rare earth elements, Cr, In, Ga, Si, Al, Ti, Zr, and the like, may be added to the Mo-containing liquid and/or the Bi-containing liquid within ranges whereby precipitates are not generated. In addition, these raw materials may be added to the Mo—Bi-containing liquid obtained by mixing the two liquids. From the perspective of precipitates being unlikely to be generated, raw materials for metals other than Mo are preferably added to the Bi-containing liquid, and it is particularly preferable for raw materials for metals other than Si, Al, Ti and Zr to be added to the Bi-containing liquid.

Next, the obtained Mo-containing liquid and Bi-containing liquid are mixed (step (ii)). Here, the Mo-containing liquid and the Bi-containing liquid are continuously supplied to the first and second flow paths, respectively, and the first flow path and second flow path are merged at a position downstream from the positions, where the Mo-containing liquid and Bi-containing liquid are supplied respectively, thereby mixing the Mo-containing liquid and the Bi-containing liquid.

The manner in which the Mo-containing liquid and Bi-containing liquid are supplied to the flow paths is preferably such that the molar supply ratio of Mo and Bi broadly matches the atomic number ratio of Mo and Bi in compositional formula (1) of the produced metal oxide catalyst, that is, p/12, for example, it is preferable for the molar supply ratio to fall within the range $(p/12) \times 0.8$ to $(p/12) \times 1.2$.

That is, in step (ii), if the molar supply rates of the Mo-containing liquid and the Bi-containing liquid to the first flow path and the second flow path (that is, the molar supply rate of Mo and the molar supply rate of Bi) are denoted by $m\alpha$ (mol/min) and $m\beta$ (mol/min) respectively, it is preferable for the Mo-containing liquid and the Bi-containing liquid so be supplied in such a way as to satisfy formula (4) below.

$$(m\beta/m\alpha)/(p/12)=0.8 \text{ to } 1.2 \quad (4)$$

Moreover, in the case of a batch type system in which step (i) and step (ii) are carried out in batches and the entire amount of a batch of the Mo—Bi-containing liquid obtained in step (ii) is stored in step (v) or in step (iv) and then step (v), and then supplied for (iii), the liquids are preferably supplied in such a way that the ratio of the mass supply rate mB (g/min) of the Bi-containing liquid relative to the mass supply rate mA (g/min) of the Mo-containing liquid to the first flow path (hereinafter also referred to as "the supply ratio") is 0.5 times to 1.5 times the ratio of the total supplied amount MB (g) of Bi-containing liquid per batch relative to the total supplied amount MA (g) of Mo-containing liquid per batch (hereinafter also referred to as "the mass ratio").

That is, the Mo-containing liquid and Bi-containing liquid are preferably supplied in such a way as to satisfy formula (3) below.

$$(mB/mA)/(MB/MA)=0.5 \text{ to } 1.5 \quad (3)$$

If the supply ratio is 0.5 times to 1.5 times the mass ratio, it is possible to further increase the uniformity of composition at the surface of the metal oxide catalyst. The value of (mB/mA)/(MB/MA) is more preferably 0.8 to 1.2, and is particularly preferably 1.0.

Explanations will now be given of the supply ratio (mB/mA) and mass ratio (MB/MA) mentioned above by giving specific examples.

The composition of the produced catalyst is one in which p=1 in formula (1) (12 atoms of Mo relative to 1 atom of Bi), one batch of Mo-containing liquid prepared in step (i) contains the required amount of Mo raw material, the entire amount (MA) of this batch is 100 parts by mass, one batch of Bi-containing liquid prepared in step (i) contains the required amount of Bi raw material (1/12th the molar amount of the Mo-containing liquid), and the entire amount (MB) of this batch is 50 parts by mass.

If these two liquids are supplied at a Mo-containing liquid:Bi-containing liquid ratio of 100:50, which represents the ratio of the supplied masses per unit time (mass supply rates) (g/min), the mass ratio and supply ratio are as follows.

Mass ratio (MB/MA)=50/100=0.5

Supply ratio (mB/mA)=50/100=0.5

Therefore, this case corresponds to one in which the mass ratio is 1.0 times the supply ratio.

Similarly, a case in which the Mo-containing liquid:Bi-containing liquid are supplied at a ratio of 100:25 (mass supply rate ratio) corresponds to one in which the supply ratio is 0.5 times the mass ratio (0.5). A case in which the Mo-containing liquid and the Bi-containing liquid are supplied at a Mo-containing liquid:Bi-containing liquid ratio of 100:75 (mass supply rate ratio) (supply ratio=75/100=0.75) corresponds to a case in which the supply ratio is 1.5 times the mass ratio (0.5).

In a case in which the supply ratio is 1.0 times the mass ratio, which is a particularly preferred embodiment, by supplying the two liquids at the same ratio as the ratio of the entire supplied amount of one batch of Bi-containing liquid relative to the entire supplied amount of one batch of Mo-containing liquid and merging the liquids in step (ii), the molar supply ratio of Mo and Bi is identical to the molar ratio of Mo and Bi in compositional formula (1) of the produced catalyst, that is, p/12.

When preparing a slurry in a conventional metal oxide catalyst production method, a Mo-containing liquid and a Bi-containing liquid are mixed by adding one of the liquids to the other liquid. In this method, however, the concentration of the component being added decreases immediately after the start of mixing and then gradually increases as the addition progresses. In this way, the desired atomic ratio is achieved once the two liquids have been completely added, but a significant imbalance readily occurs between the concentration of the component being added and the concentration of the component being added to during the addition. According to research by the inventors of the present invention, it was understood that this imbalance between the concentrations of Bi and Mo in the mixed liquid when the slurry is being prepared is a cause of a decrease in uniformity of composition at the surface of the metal oxide particles produced from the thus prepared slurry.

Conversely, because the two liquids are simultaneously supplied at the merging part in the first production method, there is little imbalance in the concentrations of the components in the mixed liquid.

In particular, in cases where the Mo-containing liquid and Bi-containing liquid are supplied within the specified ratio ranges, a slurry is formed in which the atomic ratios of Mo and Bi in the mixed liquid are close to the atomic ratios in the composition of the produced catalyst at any stage during the step where the liquids are mixed. By preparing a slurry in such a state, it is possible to better unify the compositional ratio of Mo and Bi at the surface of the ultimately produced catalyst particles.

In the first production method, in the case of a batch type system in which step (i) and step (ii) are carried out in batches and the entire amount of a batch of the Mo—Bi-containing liquid obtained in step (ii) is stored in step (v) or in step (iv) and then step (v), and then supplied for (iii), it is preferable for the supply ratio (mB/mA) to be 0.5 times to 1.5 times the mass ratio (MB/MA), as mentioned above. However, it is not necessarily essential for the entire amounts of the two liquids to come into contact within the range of 0.5 times to 1.5 times the mass ratio, and it is possible to supply the Mo-containing liquid and a part of the Bi-containing liquid in such a way as to fall outside the range mentioned above.

Specifically, it is preferable to supply 60 mass % or more of the total supplied amount of one batch of the Mo-containing liquid and Bi-containing liquid in such a way that the supply ratio is 0.5 times to 1.5 times the mass ratio, more preferable to supply 80 mass % or more of the total supplied amount of one batch of the Mo-containing liquid and Bi-containing liquid in such a way that the supply ratio is 0.5 times to 1.5 times the mass ratio, and particularly preferable to supply 100 mass % of the total supplied amount of one batch of the Mo-containing liquid and Bi-containing liquid (that is, across the whole of step (ii)) in such a way that the supply ratio is 0.5 times to 1.5 times the mass ratio.

This is explained above in an example in which the amount of the Mo-containing liquid containing a raw material having 12 atoms' worth of Mo is 100 parts by mass and the amount of the Bi-containing liquid containing a raw material having 1 atom's worth of Bi is 50 parts by mass. In this case, the total supplied amount of the Mo-containing liquid and the Bi-containing liquid is 150 parts by mass, and 60 mass % or more of this corresponds to 90 parts by mass or more.

That is, supplying 60 mass % or more of the total supplied amount of the two liquids so that the supply ratio is 0.5 times to 1.5 times the mass ratio represents the ratio of the supplied amount per unit time (the mass supply rate), and corresponds to bringing a total of 90 parts by mass or more of the two liquids into contact so that the Mo-containing liquid:Bi-containing liquid ratio falls within the range 100:25 to 100:75.

In step (ii), the merging temperature at which the two liquids are merged is preferably 5° C. to 98° C. This merging temperature is more preferably 35° C. to 98° C., further preferably 35° C. to 80° C., and particularly preferably 35° C. to 60° C. By merging the liquids at 35° C. to 60° C., it is possible to produce catalyst particles having a more uniform surface composition. Here, the merging temperature means the liquid temperature at the part where the two liquids merge, and can be measured using a temperature gauge.

In cases where a step of further mixing the Mo—Bi-containing liquid is provided after producing the Mo—Bi-containing liquid (slurry) by mixing the two liquids in step (ii) but before drying the Mo—Bi-containing liquid (step (iv)), the method for further mixing the produced Mo—Bi-containing liquid is not particularly limited, and examples of this method include passing the Mo—Bi-containing liquid through a static mixing device and stirring the Mo—Bi-containing liquid using a stirrer.

The stirring temperature is preferably similar to the merging temperature when the two liquids are merged and, more specifically, is preferably 35° C. to 80° C.

In the present embodiment, the configuration of the apparatus used to produce the metal oxide catalyst is not particularly limited, but the apparatus preferably has, for example, a first flow path for supplying the Mo-containing liquid, a second flow path for supplying the Bi-containing liquid, and a merging part where the first flow path and second flow path merge.

Means for supplying the Mo-containing liquid and Bi-containing liquid to the first flow path and second flow path are not particularly limited, and it is preferable to use, for example, quantitative feeders. By using quantitative feeders, the two liquids can be supplied at more precise ratios. The quantitative feeders are not particularly limited, but quantitative delivery pumps are preferred.

The merging part where the two liquids merge is not particularly limited as long as the two liquids can merge, but it is possible to use, for example, a Y-shaped or T-shaped pipe. The cross-sectional shape of the pipe may be round (a cylindrical pipe), and it is preferable to provide a mechanism or inserted object that facilitates mixing of the Mo—Bi-containing liquid in the pipe. The angle at which the two liquids are merged may be parallel, perpendicular or opposing.

Figure 1:
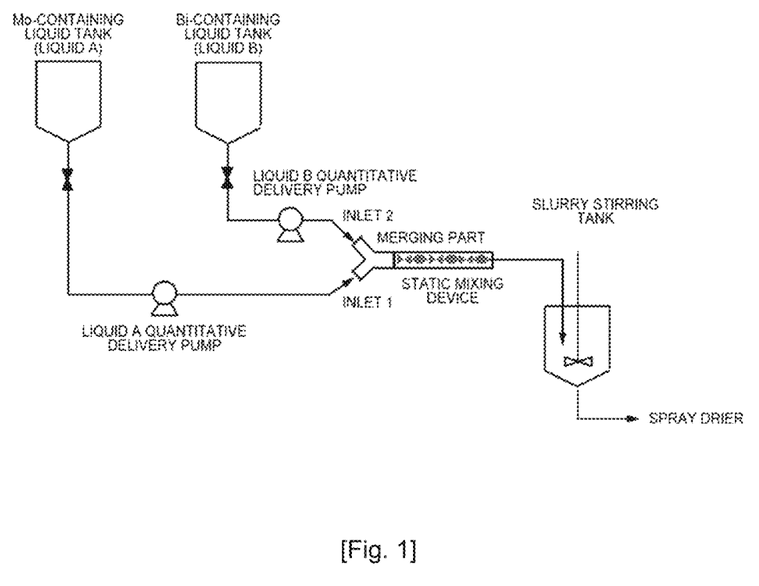
FIG. 1 is a conceptual diagram that shows an example of an apparatus for producing the metal oxide catalyst according to the present invention.

It is preferable to provide a mixing device for further mixing the Mo—Bi-containing liquid at a position downstream of the merging part. One example of a mixing device is a stirring tank having a stirrer. One example of this type of device is shown in FIG. 1. Moreover, it is preferable for the apparatus mentioned above to have an insulating or heating mechanism, such as a hot water jacket able to maintain the desired temperature.

Figure 2:
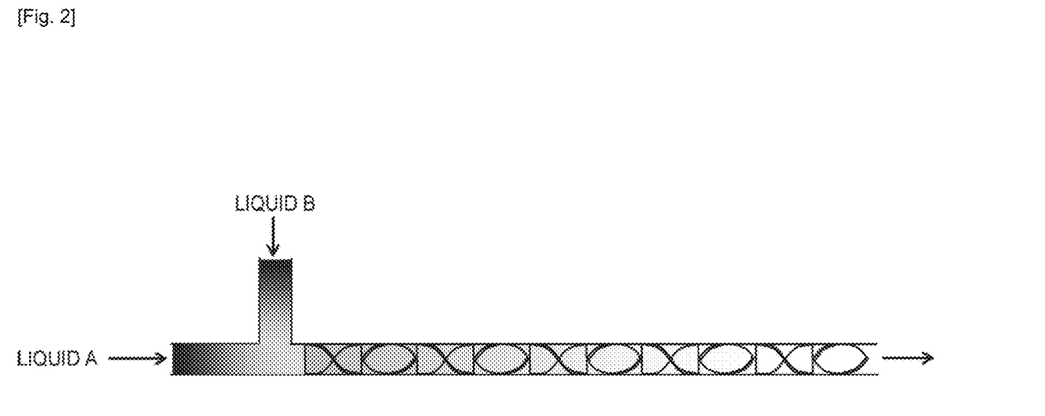
FIG. 2 is a schematic view that shows an example of a static mixing device.

In addition, another example of a mixing device is a static mixing device such as that shown in FIG. 2 (the main members of this mixing device are a pipe and twisted plates fixed in the pipe, and fluids supplied to the pipe are mixed by caused to flow along the surfaces of the twisted plates). One example of a static mixing device is a static mixer (available from Noritake Co., Limited).

By drying the thus produced Mo—Bi-containing liquid (step (iii)) it is possible to form a metal oxide catalyst having the bulk composition represented by formula (1).

It is preferable for the Mo—Bi-containing liquid to have a pH of 3 or lower prior to being dried. This pH is more preferably 2 or less, and further preferably 1 or less. The pH can be adjusted by, for example, adjusting the amount of acidic solution added to the raw materials. If the pH is 3 or lower, it is possible to suppress an increase in the viscosity of the Mo—Bi-containing liquid, and the Mo—Bi-containing liquid can be stably supplied to the subsequent drying step (iii).

Because the slurry preparation steps for forming the catalyst precursor can all be carried out in a liquid phase in the first method, it can be said that the first method is extremely simple compared to a method in which drying, firing, pulverization, and the like, are required to form a catalyst precursor.

In step (iii), the drying method is not particularly limited, but it is preferable to obtain dry particles by spray drying the Mo—Bi-containing liquid. For the spray drying, it is preferable to use a spray dryer, such as one used in industrial applications.

In the spray drying step, the Mo—Bi-containing liquid is first atomized. The atomizing method is not particularly limited, but examples thereof include centrifugal systems, two-fluid nozzle systems and high pressure nozzle systems. A centrifugal system is particularly preferred from the perspective of not causing nozzle clogging and the like.

The method for drying droplets of the atomized Mo—Bi-containing liquid is not particularly limited, but it is preferable to dry the droplets by means of a hot air current in a spray dryer. In such cases, it is preferable for the hot air current inlet temperature to be 100° C. to 400° C. and the hot air current outlet temperature to be 150° C. to 300° C.

Moreover, when atomizing the liquid, it is preferable to adjust the spraying device so that the diameters of the sprayed particles fall within the desired range according to the particle diameter of the target catalyst. For example, because the average particle diameter of the catalyst is preferably approximately 10 to 150 μm in cases where the catalyst is to be used in a fluidized bed reaction, the rotational speed of the atomizing device (atomizer) is selected as appropriate so as to achieve an average particle diameter that falls within this range. In general, a higher atomizer rotational speed leads to a smaller average particle diameter.

In the present embodiment, it is preferable to include a firing step for obtaining a metal oxide catalyst by firing the dried product (dried particles) obtained in the drying step. The firing method is not particularly limited, but examples thereof include static firing, fluidized firing and rotary furnace firing. From the perspective of being able to uniformly fire the particles, rotary furnace firing using a rotary kiln is preferred. The firing temperature is preferably 400° C. to 800° C., more preferably 500° C. to 750° C., and further preferably 550° C. to 700° C. The firing time is preferably 1 to 24 hours, and more preferably 2 to 8 hours. Conditions such as firing temperature and firing time are selected as appropriate in order to achieve the desired catalyst physical properties and reaction performance. It is preferable to carry out preliminary firing at a temperature of 250° C. to 420° C., and then firing under the conditions described above.

In the present embodiment, by carrying out the Mo—Bi-containing liquid preparation steps (steps (i) and (ii)), the mixing step (step (iv)) and storage step (step (v)) as required, the drying step (step (iii)) and, if necessary, the firing step as a series of processes, a catalyst having stable catalyst physical properties and catalytic performance can be produced rapidly and continuously.

In the present embodiment, in cases where both step (iv) and step (v) are carried out between step (ii) and step (iii), it is preferable to carry out step (iv) and then step (v), or to carry out step (iv) and step (v) simultaneously (that is, storing the Mo—Bi-containing liquid under stirring).

In addition, in the case of a batch processing system in which steps (i), (ii) and (v) or steps (i), (ii), (iv) and (v) are carried out as a series of processes, it is preferable for the amount stored in step (v) to be the entire amount of the Mo—Bi-containing liquid obtained in step (ii). By temporarily storing the entire amount of the Mo—Bi-containing liquid prepared in step (ii), it is possible to make the ratio of the number of atoms of Mo and Bi in the Mo—Bi-containing liquid supplied for (iii) equal to the ratio of the number of atoms of Mo and Bi in formula (1) even in cases where the supplied amounts of the Mo-containing liquid and Bi-containing liquid in step (ii) vary, and it is also possible to make the composition of the obtained catalyst particles similar to the target composition.

The storage vessel is not particularly limited, and it is possible to carry out step (v) and step (iv) simultaneously using, for example, a vessel having a stirring mechanism as the storage vessel.

Moreover, when obtaining the metal oxide catalyst of the present embodiment, use of the production method of the present embodiment (the first production method) is preferred due to this production method being unaffected by the scale of the produced catalyst, but the metal oxide catalyst of the present embodiment may be produced using a method other than the first production method.

For example, as shown in Working Example 9 below, even in cases where a stirring and mixing tank is used to prepare the raw material slurry and batch mixing of the Mo-containing liquid and Bi-containing liquid is carried out by introducing one of the liquids into the other liquid, it is possible to produce at least 50 kg of metal oxide catalyst per batch, and by setting the period of time over which the liquid being introduced is introduced to be not more than 8 minutes, and preferably not more than 4 minutes, it is possible to promote uniform mixing of the two liquids and obtain the metal oxide catalyst of the present embodiment (a second production method).

This is thought to be because the mass of liquid introduced is increased by increasing the amount of Mo—Bi-containing liquid introduced, and more uniform mixing of the slurry can be achieved as a result of a synergistic effect achieved by increasing the energy of impact with the liquid being introduced and treating for a short period of time.

<Method for Producing Butadiene from n-Butene>

The metal oxide catalyst of the present embodiment can be used when producing a conjugated diolefin (for example, 1,3-butadiene) by means of an oxidative dehydrogenation reaction between a monoolefin having 4 or more carbon atoms (for example, n-butene) and molecular oxygen.

A conjugated diolefin can be produced by subjecting a monoolefin an oxidative dehydrogenation reaction in the presence of the metal oxide catalyst, and this reaction system may be a fluidized bed system or a fixed bed system. The reaction is preferably carried out using a fluidized bed system from the perspectives of localized heat storage caused by reaction heat being unlikely to occur, being able to increase the concentration of n-butene in a raw material gas and being able to increase productivity.

In a method for producing a conjugated diolefin using the metal oxide catalyst of the present embodiment, a monoolefin having 4 or more carbon atoms and molecular oxygen are used as raw materials.

Monoolefins are organic compounds which have only one carbon-carbon double bond in the molecule and which generally do not have a functional group, and are straight-chain and/or branched chain hydrocarbons. The upper limit for the number of carbon atoms is not particularly limited, but is preferably 6 or less from the perspective of reactivity. Examples of monoolefins having 4 or more carbon atoms include n-butene (1-butene and 2-butene), 1-pentene, 2-pentene, isopentene (2-methyl-1-butene and 3-methyl-1-butene), 1-hexene, 2-hexene and 2,3-dimethylbutene. Of these, it is preferable to use n-butene or isopentene as the monoolefin from the perspective of product flexibility. It is possible to use one type of monoolefin as a raw material, or a combination of two or more types of monoolefin.

The monoolefin does not necessarily need to have a high purity, and it is possible to use a mixture of monoolefins or an industrial grade monoolefin. For example, in the case of n-butene, it is possible to use a residual component obtained following recovery of butadiene from a $C_4$ fraction that is by-produced in naphtha pyrolysis (raffinate 1), a residual component obtained following further recovery of isobutylene from this residual component (raffinate 2), a butane fraction obtained by subjecting n-butene to a dehydrogenation reaction or oxidative dehydrogenation reaction, a $C_4$ fraction that is by-produced from a catalytic conversion reaction of ethylene obtained by means of ethane pyrolysis or dehydration of biomass ethanol, or n-butene obtained by dimerization of ethylene. Biomass ethanol is ethanol obtained from plant resources, and specific examples thereof include ethanol obtained by fermentation of sugar cane, corn, or the like, and ethanol obtained from wood resources such as waste materials, timber from thinned forests, rice straw and agricultural produce.

The monoolefin may contain paraffin that are inert in the oxidative dehydrogenation reaction between the monoolefin and air. Examples of paraffin include methane, ethane, propane, butane, pentane, hexane, heptane, octane and nonane. In addition, it is possible to separate butadiene, isoprene, and the like, which are target products, from the reaction product gas of the oxidative dehydrogenation reaction between the monoolefin and air, mix at least a part of the monoolefin, such as unreacted butene or isopentene, with a monoolefin to be supplied to the reactor, and carry out the reaction again.

Molecular oxygen is preferably supplied to the reactor as an oxygen-containing gas, and the oxygen-containing gas may contain nitrogen, helium, water vapor, $CO_2$, CO, and the like, in addition to oxygen. It is preferable to use air as the oxygen-containing gas.

In addition, it is preferable for the monoolefin to be supplied to the reactor as a monoolefin-containing gas, and in the case of a monoolefin that is not a gas at normal pressure and a temperature of approximately 5° C. to 35° C., it is preferable to gasify the monoolefin using a gasification device having a heating mechanism such as steam or a heat transfer coil, and then supply the monoolefin to the reactor.

From the perspective of conjugated diolefin productivity, the concentration of the monoolefin supplied to the reactor is such that the concentration of the monoolefin in the raw material gas as a whole (the total amount of the monoolefin-containing gas and the oxygen-containing gas) is preferably 2 to 30 vol %, and more preferably 3 to 25 vol %.

The method for supplying the monoolefin-containing gas and the oxygen-containing gas is not limited, and it is possible to mix both gases in advance and then supply the mixture to the reactor, or supply the gases separately to the reactor.

The reaction temperature is preferably 300° C. to 500° C., and more preferably 300° C. to 420° C.

The reaction pressure is preferably between −0.1 MPa (gauge pressure) and 0.5 MPa (gauge pressure), and more preferably between normal pressure and 0.1 MPa (gauge pressure).

When producing a conjugated diolefin, the contact time between the catalyst and the raw material gas as a whole, as defined using the formula below, is preferably 0.5 (g·sec/cc) to 5.0 (g·sec/cc), and more preferably 0.7 (g·sec/cc) to 3.5 (g·sec/cc).

Contact time (g·sec/cc)=$W/F \times 60 \times 273.15/(273.15+T) \times (P \times 1000+101.325)/101.325$

[In the formula, W denotes the filled amount of catalyst (g), F denotes the amount of raw material gas as a whole (cc/min), T denotes the reaction temperature (° C.), and P denotes the reaction pressure (MPa (gauge pressure))].

The oxygen concentration in the generated gas at the reactor outlet is preferably 0.02 to 3 vol %, more preferably 0.2 to 2 vol %, and further preferably 0.9 to 1.5 vol %.

An example of one aspect of an industrial reactor able to be used is, in the case of a fluidized bed reaction, a bubble fluidized bed reactor which has a raw material gas disperser, an inserted object and a cyclone as principal constituent elements in the reactor and in which a metal oxide catalyst is fluidized inside the reactor while being brought into contact with the raw material gas. An example of one aspect of an industrial reactor able to be used in the case of a fixed bed reaction is a multi-tubular fixed bed reactor which has a multiplicity of reaction tubes and an external heat medium circulation device and in which the raw material gas flows upwards or downwards in the reaction tubes and is brought into contact with a molded metal oxide catalyst.

WORKING EXAMPLES

The present embodiment will now be explained in greater details by means of working examples, but the present embodiment is not limited to the working examples given below.

<n-Butene Conversion Rate and Butadiene Yield>

In the working examples and comparative examples, the n-butene conversion rate and butadiene yield, which are used to indicate reaction performance (catalyst performance), are defined by the formulae below.

n-butene conversion rate (%)=(number of moles of n-butene reacted)/(number of moles of n-butene supplied)×100

Butadiene yield (%)=(number of moles of butadiene produced)/(number of moles of n-butene supplied)×100

Moreover, the number of moles of reacted n-butene was calculated by subtracting the number of moles of unreacted n-butene remaining in the reaction product gas from the number of moles of supplied n-butene, and the number of moles of butadiene and unreacted n-butene in the reaction product gas was analyzed by means of gas chromatography (using a GC2010 Plus available from Shimadzu Corporation, detectors: TCD and FID).

<Evaluation of Uniformity of Composition at Metal Oxide Catalyst Particle Surface>

The uniformity of composition at the surface of particles of the metal oxide catalysts obtained in the working examples and comparative examples was evaluated in the manner described below, and expressed as standard deviation in terms of composition at particle surfaces.

A small amount of catalyst powder (fired powder) was placed on platform of a SEM-EDX (Scanning Electron Microscopes-Energy Dispersive X-ray Spectroscopy) composition analyzer (SEM: SU-70 available from Hitachi, Ltd., EDX: EMAX/X-max available from Horiba, Ltd.), 100 randomly selected catalyst particles in which the true circle-equivalent diameter (the diameter of a true circle having the same area) in a particle image is ±10 μm of the average particle diameter (40 to 60 μm in this case), as determined using a particle size distribution analyzer (Microtrac MT300 available from Nikkiso Co., Ltd.), were measured in terms of Mo molar concentration and Bi molar concentration in a particle surface area measuring 10 μm×10 μm (magnification 1500 times, accelerating voltage 20 kV), and the ratio $(Bi/Mo)_{surf}$ of Bi concentration relative to Mo concentration at the surface of the catalyst particles was determined.

Next, 20 mg of the same catalyst powder was weighed out, dissolved in aqueous nitrohydrochloric acid at a temperature of 210° C., and diluted within the measurement range using ultrapure water, and the concentration of constituent atoms was measured using ICP emission spectroscopic analysis (using an SPS3500DD available from Seiko Instruments Inc.), and the bulk composition was calculated and the ratio $(Bi/Mo)_{bulk}$ of Bi concentration relative to Mo concentration in the catalyst bulk was determined. Moreover, in all of Catalysts 1 to 13 described below, the bulk composition, that is, the ratio of elements constituting the catalyst relative to molybdenum (including the Mo molar concentration and Bi molar concentration in the catalyst bulk) was identical to the theoretical value calculated from the charged masses of raw materials (in a molar composition expressed on the basis of $Mo_{12}$, the bulk composition was identical to the charged mass ratio to the first two digits).

A value obtained by dividing the $(Bi/Mo)_{surf}$ value for each of 100 particles by the $(Bi/Mo)_{bulk}$ value was denoted by $S_k$ (k=1 to 100), the average value p of the 100 $S_k$ values was calculated, and the standard deviation was determined from formula (2).

$$\text{Standard deviation} = \{((S_1-\mu)^2+(S_2-\mu)^2+ \ldots + (S_{100}-\mu)^2)/100[\text{number}]\}^{1/2} \quad (2)$$

Working Example 1

[Production of Catalyst 1]

A metal oxide catalyst was produced in the manner described below by adjusting the charged masses of raw materials so as to obtain the composition $Mo_{12}Bi_{0.8}Fe_{2.5}Ni_{4.6}K_{0.12}Rb_{0.05}Mg_{1.1}Ce_{1.5}Si_{45.9}O_x$.

1032 g of ammonium molybdate tetrahydrate was dissolved in 1841 g of pure water. 3922 g of a 34 mass % silica sol containing $SiO_2$ having an average particle diameter of 12 nm and 523 g of pure water were added to this liquid. To this was added a liquid obtained by dissolving 80 g of oxalic acid in 533 g of pure water. The total amount thereof was 7931 g (Mo-containing liquid. Hereinafter referred to as "Liquid A1").

190 g of bismuth nitrate pentahydrate, 317 g of cerium nitrate hexahydrate, 489 g of ferric nitrate nonahydrate, 659 g of nickel nitrate hexahydrate, 139 g of magnesium nitrate hexahydrate, 5.9 g of potassium nitrate and 3.6 g of rubidium nitrate were dissolved in 1041 g of a 16.6 mass % nitric acid solution. The total amount thereof was 2845 g (Bi-containing liquid. Hereinafter referred to as "Liquid B1").

A container containing Liquid A1 was connected, via a Liquid A1 quantitative delivery pump, to one inlet port 1 of an empty Y-shaped stainless steel cylindrical pipe (internal diameter 15 mm, length 300 mm) (a merging part) by a pipe (a first flow path). In addition, a container containing Liquid B1 was connected, via a Liquid B1 quantitative delivery pump, to another inlet port 2 of the Y-shaped pipe by a pipe (a second flow path). The outlet port of this Y-shaped pipe was connected to a static mixing device (a static mixer) having a screw type internal object, and an outlet port of the static mixing device was connected via a pipe to a slurry stirring tank having a stirrer. A schematic view of this apparatus is shown in FIG. 1.

Liquid A1, which was held at 50° C., was supplied to the Y-shaped pipe at a flow rate of 793 (g/min) using the Liquid A1 quantitative delivery pump while simultaneously supplying Liquid B1, which was held at 50° C., at a flow rate of 285 (g/min) using the Liquid B1 quantitative delivery pump, and the two liquids were brought into contact with each other in the same direction (parallel flow) in the Y-shaped pipe and the static mixing device. A Mo—Bi-containing liquid was prepared as a slurry by carrying out this procedure for 10 minutes. Here, the supply ratio of Liquid B1 [Bi-containing liquid] to Liquid A1 [Mo-containing liquid] was 285 (g/min)/793 (g/min)=0.36, and the mass ratio of the total amount of the Bi-containing liquid relative to the total amount of the Mo-containing liquid was 2845 (g)/7931 (g)=1.0 times 0.36. All of Liquid A1 and Liquid B1 (100 mass %) were merged at this supply ratio. Here, the merging temperature was 50° C.

The entire amount of this Mo—Bi-containing liquid was stored in a slurry stirring tank provided downstream of the static mixing device, and stirring was continued for a further 1 hour at 50° C. after the two liquids had been fully supplied. This Mo—Bi-containing liquid had a pH of 1 or lower and was in the form of a slurry prior to being spray dried.

Next, a dry powder was obtained by spray drying this Mo—Bi-containing liquid using a spray drier (an OC-16 available from Ohkawara Kakohki Co., Ltd.). Moreover, the hot air current inlet temperature was 250° C. and the hot air current outlet temperature was 140° C.

A catalyst (Catalyst 1) was obtained by firing the obtained dry powder for 2 hours at 590° C. using a rotary kiln (an RK125140 available from Nikkato Corporation, firing tube internal diameter: 80 mm, firing tube length: 1500 mm, no. of barriers: 8, barrier height: 10 mm).

The obtained Catalyst 1 had an average particle diameter of 51 μm. The average particle diameter was measured using a particle size distribution analyzer. Moreover, the average particle diameters of Catalysts 1 to 13 in the working examples and comparative examples below were 45 to 55 μm.

Next, the surface Mo concentration and Bi concentration of 100 particles of this Catalyst 1 were measured by means of SEM-EDX, and the ratio $(Bi/Mo)_{surf}$ of the Bi molar concentration relative to the Mo molar concentration was determined. In addition, $(Bi/Mo)_{bulk}$ was determined from the catalyst bulk composition determined above, and $S_1 \ldots S_{100}$ were determined by dividing the $(Bi/Mo)_{surf}$ values of the 100 particles by the $(Bi/Mo)_{bulk}$. In addition, the average value p of these (the average value of $S_1 \ldots S_{100}$) was determined, and the standard deviation was determined using formula (2). The results are shown in Table 1.

[Production of Butadiene Using Catalyst 1 (Fluidized Bed Reaction)]

27 g of Catalyst 1 was filled in a PYREX® glass fluidized bed reaction tube having an internal diameter of 25.4 mm. A butadiene production reaction was carried out by flushing 1-butene as an n-butene-containing gas and oxygen and nitrogen as a molecular oxygen-containing gas into this reaction tube at a flow rate ratio of 1:8 to 1:11. The reaction temperature was 360° C. and the reaction pressure was 0.05 MPa (gauge pressure). The 1-butene concentration was 10 vol % relative to the entire amount of raw material gases, and the time of contact between Catalyst 1 and the raw material gases was 0.8 to 1.0 (g·sec/cc). The oxygen concentration at the reactor outlet was 0.8 to 1.2 vol %. Reaction results (1-butene conversion rate and butadiene yield) when a reaction was carried out for 24 hours under these reaction conditions are shown in Table 1.

Working Example 2

[Production of Catalyst 2]

A Mo-containing liquid (the same as Liquid A1, but hereinafter referred to as "Liquid A2") and a Bi-containing liquid (the same as Liquid B1, but hereinafter referred to as "Liquid B2") were produced in the same way as in Working Example 1. Because the overall supplied amount of Liquid A2 and Liquid B2 was the same as in Working Example 1, the mass ratio in this case was 0.36, as in Working Example 1.

A catalyst (Catalyst 2) was obtained in the same way as in Working Example 1, except that the supply ratio of Liquid B2 relative to Liquid A2 was varied within the range 0.8 times to 1.2 times the mass ratio mentioned above (0.36). All of Liquid A2 and Liquid B2 (100 mass %) were merged at a supply ratio within this range.

Specifically, the following procedure was carried out. Liquid A2 was supplied to the Y-shaped pipe for 3 minutes at a flow rate of 837 (g/min) via the first flow path while simultaneously supplying Liquid B2 at a flow rate of 241 (g/min) via the second flow path. This supply ratio was 241 (g/min)/837 (g/min)=0.29, which was 0.8 times the mass ratio mentioned above (0.36).

Next, the supply flow rates of Liquid A2 and Liquid B2 were altered, and Liquid A2 was supplied at a flow rate of 792 (g/min) for 4 minutes while simultaneously supplying Liquid B2 at a flow rate of 285 (g/min). This supply ratio was 285 (g/min)/792 (g/min)=0.36, which was 1.0 times the mass ratio mentioned above (0.36).

Next, the supply flow rates of Liquid A2 and Liquid B2 were altered, and Liquid A2 was supplied at a flow rate of 753 (g/min) for 3 minutes while simultaneously supplying Liquid B2 at a flow rate of 325 (g/min). This supply ratio was 325 (g/min)/753 (g/min)=0.43, which was 1.2 times the mass ratio mentioned above (0.36).

Moreover, the merging temperature for Liquid A2 and Liquid B2 was 50° C. at each stage. The thus produced Mo—Bi-containing liquid had a pH of 1 or lower and was in the form of a slurry prior to being spray dried.

[Production of Butadiene Using Catalyst 2 (Fluidized Bed Reaction)]

Butadiene was produced in the same way as in Working Example 1, except that Catalyst 2 was used instead of Catalyst 1.

The standard deviation and reaction results for Catalyst 2 are shown in Table 1.

Working Example 3

[Production of Catalyst 3]

A Mo-containing liquid (the same as Liquid A1, but hereinafter referred to as "Liquid A3") and a Bi-containing liquid (the same as Liquid B1, but hereinafter referred to as "Liquid B3") were produced in the same way as in Working Example 1. Because the overall supplied amount of Liquid A3 and Liquid B3 was the same as in Working Example 1, the mass ratio in this case was 0.36, as in Working Example 1.

A catalyst (Catalyst 3) was obtained in the same way as in Working Example 1, except that the supply ratio of Liquid B3 relative to Liquid A3 was varied within the range 0.5 times to 1.5 times the mass ratio mentioned above (0.36). All of Liquid A3 and Liquid B3 (100 mass %) were merged at a supply ratio within this range.

Specifically, the following procedure was carried out. Liquid A3 was supplied to the Y-shaped pipe for 3 minutes at a flow rate of 913 (g/min) while simultaneously supplying Liquid B2 at a flow rate of 164 (g/min). This supply ratio was 164 (g/min)/913 (g/min)=0.18, which was 0.5 times the mass ratio mentioned above (0.36).

Next, the supply flow rates of Liquid A3 and Liquid B3 were altered, and Liquid A3 was supplied at a flow rate of 792 (g/min) for 5 minutes while simultaneously supplying Liquid B3 at a flow rate of 285 (g/min). This supply ratio was 285 (g/min)/792 (g/min)=0.36, which was 1.0 times the mass ratio mentioned above (0.36).

Next, the supply flow rates of Liquid A3 and Liquid B3 were altered, and Liquid A3 was supplied at a flow rate of 700 (g/min) for 2 minutes while simultaneously supplying Liquid B3 at a flow rate of 378 (g/min). This supply ratio was 378 (g/min)/700 (g/min)=0.54, which was 1.5 times the mass ratio mentioned above (0.36). Moreover, the merging temperature for Liquid A3 and Liquid B3 was 50° C. at each stage. The thus produced Mo—Bi-containing liquid had a pH of 1 or lower and was in the form of a slurry prior to being spray dried.

[Production of Butadiene Using Catalyst 3 (Fluidized Bed Reaction)]

Butadiene was produced in the same way as in Working Example 1, except that Catalyst 3 was used instead of Catalyst 1.

The standard deviation and reaction results for Catalyst 3 are shown in Table 1.

Working Example 4

[Production of Catalyst 4]

A metal oxide catalyst was produced in the same way as in Working Example 1, except that the steps following storage of the Mo—Bi-containing liquid were carried out continuously at 600 times the scale of that in Working Example 1.

Specifically, the following procedure was carried out. A Mo-containing liquid (hereinafter referred to as "Liquid A4") and a Bi-containing liquid (hereinafter referred to as "Liquid B4") were produced at 10 times the scale in Working Example 1. Liquid A4, which was held at 50° C., was supplied to the Y-shaped pipe at a flow rate of 793 (g/min) using the Liquid A4 quantitative delivery pump while simultaneously supplying Liquid B4, which was held at 50° C., at a flow rate of 285 (g/min) using the Liquid B4 quantitative delivery pump, and the two liquids were brought into contact in the same direction (parallel flow) in the Y-shaped pipe and the static mixing device. Here, the molar supply rates were 7×10320 (g)/1235.85 (g/mol)×793 (g/min)/79310 (g)=0.58 (mol/min) for Mo, and 1900 (g)/485.07 (g/mol)×285 (g/min)/28450 (g)=0.039 (mol/min) for Bi, and the molar supply ratio of Bi atoms relative to Mo atoms was 0.039 (mol/min)/0.58 (mol/min) =0.067.

This is 1.0 times the molar ratio in the compositional formula (0.8/12=0.067).

Moreover, the merging temperature for Liquid A4 and Liquid B4 was 50° C.

Preparation of the Mo—Bi-containing liquid mentioned above was repeated 60 times, with no intervals between preparations, the produced Mo—Bi-containing liquids were stored sequentially in a slurry stirring tank (liquid temperature 50° C., 300 rpm) provided downstream of the outlet side of the static mixing device, and 1 hour after the storage started, the Mo—Bi-containing liquid was fed to a spray drier and sprayed. This slurry had a pH of 1 or lower and was in the form of a slurry prior to being spray dried.

Spray drying and firing conditions were the same as in Working Example 1, except that the spray drier used for the spray drying had a hot air current inlet temperature of 320° C. and a hot air current outlet temperature of 230° C., and the firing temperature of the rotary kiln was 600° C. A catalyst was removed 100 hours after the start of catalyst production, and this catalyst was referred to as Catalyst 4.

[Production of Butadiene Using Catalyst 4 (Fluidized Bed Reaction)]

Butadiene was produced in the same way as in Working Example 1, except that Catalyst 4 was used instead of Catalyst 1.

The standard deviation and reaction results for Catalyst 4 are shown in Table 1.

Working Example 5

[Production of Catalyst 5]

A catalyst (Catalyst 5) was obtained in the same way as in Working Example 1, except that the Mo-containing liquid and the Bi-containing liquid were mixed in the Y-shaped pipe and the static mixing device, and then fed directly to the spray drier without being stored in the slurry stirring tank. Moreover, the merging temperature was 50° C. The thus produced Mo—Bi-containing liquid had a pH of 1 or lower and was in the form of a slurry prior to being spray dried.

[Production of Butadiene Using Catalyst 5 (Fluidized Bed Reaction)]

Butadiene was produced in the same way as in Working Example 1, except that Catalyst 5 was used instead of Catalyst 1.

The standard deviation and reaction results for Catalyst 5 are shown in Table 1.

Working Example 6

[Production of Catalyst 6]

A metal oxide catalyst was produced in the manner described below by adjusting the charged masses of raw materials so as to obtain the composition $Mo_{12}Bi_{1.0}Fe_{1.6}Ni_{2.0}Co_{3.0}Rb_{0.21}Mg_{1.3}Ce_{2.0}Si_{20.4}O_x$.

1391 g of ammonium molybdate tetrahydrate was dissolved in 2484 g of pure water. 2353 g of a 34 mass % silica sol containing $SiO_2$ having an average particle diameter of 12 nm and 314 g of pure water were added to this liquid. 20 g of rubidium nitrate was also added. The total amount thereof was 6562 g (Mo-containing liquid. Hereinafter referred to as "Liquid A6").

320 g of bismuth nitrate pentahydrate, 570 g of cerium nitrate hexahydrate, 422 g of ferric nitrate nonahydrate, 386 g of nickel nitrate hexahydrate, 581 g of cobalt nitrate hexahydrate and 221 g of magnesium nitrate hexahydrate were dissolved in 600 g of a 16.6 mass % nitric acid solution. 1034 g of pure water was also added. The total amount thereof was 4134 g (Bi-containing liquid. Hereinafter referred to as "Liquid B6").

The mass ratio in this case was 4134 (g)/6562 (g)=0.63.

Liquid A6, which was held at 98° C., and Liquid B6, which was held at 98° C., were fed by means of metering pumps to an inlet 1 and an inlet 2, respectively, of a T-shaped stainless steel cylindrical pipe (no inserted object, internal diameter 15 mm, length 300 mm) (merging part), and the two liquids were merged perpendicularly at an angle of 90°. The thus produced Mo—Bi-containing liquid was fed from the outlet of the T-shaped pipe into a slurry stirring tank. This procedure was carried out for 10 minutes. During this period, the supply ratio was altered within the range 0.5 times to 1.4 times the mass ratio mentioned above (0.63), and all of Liquid A6 and Liquid B6 (100 mass %) were merged.

Specifically, the following procedure was carried out.

Liquid A6 was supplied via a pipe to the T-shaped pipe for 3 minutes at a flow rate of 820 (g/min) while simultaneously supplying Liquid B6 at a flow rate of 256 (g/min) via a pipe. This supply ratio was 256 (g/min)/820 (g/min)=0.31, which was 0.5 times the mass ratio mentioned above (0.63).

Next, the supply flow rates of Liquid A6 and Liquid B6 were altered, and Liquid A6 was supplied at a flow rate of 656 (g/min) for 2 minutes while simultaneously supplying Liquid B6 at a flow rate of 413 (g/min). This supply ratio was 413 (g/min)/656 (g/min)=0.63, which was 1.0 times the mass ratio mentioned above (0.63).

Next, the supply flow rates of Liquid A6 and Liquid B6 were altered, and Liquid A6 was supplied at a flow rate of 558 (g/min) for 5 minutes while simultaneously supplying Liquid B6 at a flow rate of 508 (g/min). This supply ratio was 508 (g/min)/558 (g/min)=0.91, which was 1.4 times the mass ratio mentioned above (0.63).

Moreover, the merging temperature for Liquid A6 and Liquid B6 was 98° C. at each stage. The Mo—Bi-containing liquid produced in the T-shaped pipe was stirred for a further 10 minutes at 98° C. in the slurry stirring tank.

Hereinafter, a catalyst (Catalyst 6) was obtained in the same way as in Working Example 1. This Mo—Bi-containing liquid had a pH of 1 or lower and was in the form of a slurry prior to being spray dried. The standard deviation for Catalyst 6 is shown in Table 1.

[Production of Butadiene Using Catalyst 6 (Fixed Bed Reaction)]

Catalyst 6 was molded using a ring-shaped tablet-forming machine (height 4 mm, external diameter 5 mm, internal diameter 2 mm). The breaking hardness of this ring-shaped molded catalyst was measured in the usual manner using Kiya type hardness tester. The breaking hardness was 5.2 kg, which was sufficiently hard for industrial applications. 25 g of this molded catalyst was filled in a PYREX® glass fixed bed reaction tube having an internal diameter of 25.4 mm. Raw material gases comprising 1-butene, oxygen and nitrogen were fed into this reaction tube, and a butadiene production reaction was carried out. The reaction temperature was 360° C. and the reaction pressure was 0.05 MPa (gauge pressure). The 1-butene concentration and 2-butene concentration in the n-butene-containing gas were 8 vol % and 2 vol %, respectively, relative to entire amount of the raw material gases, and the contact time was 0.8 to 2.0 (g·sec/cc). The oxygen concentration at the reactor outlet was 0.8 to 1.2 vol %. Reaction results when a reaction was carried out for 24 hours under these reaction conditions are shown in Table 1.

Working Example 7

[Production of Catalyst 7]

A metal oxide catalyst was produced in the manner described below by adjusting the charged masses of raw materials so as to obtain the composition $Mo_{12}Bi_{0.4}Fe_{2.3}Ni_{2.5}Co_{2.5}Cr_{0.02}Rb_{0.08}K_{0.06}Mg_{1.6}Ce_{1.2}Si_{29.4}O_x$.

1288 g of ammonium molybdate tetrahydrate was dissolved in 2298 g of pure water. 2980 g of a 34 mass % silica sol containing $SiO_2$ having an average particle diameter of 12 nm, 133 g of a 41 mass % silica sol containing $SiO_2$ having an average particle diameter of 40 nm, and 442 g of pure water were added to this liquid. 7 g of rubidium nitrate and 4 g of potassium nitrate were also added. The total amount thereof was 7152 g (Mo-containing liquid. Hereinafter referred to as "Liquid A7").

118 g of bismuth nitrate pentahydrate, 316 g of cerium nitrate hexahydrate, 562 g of ferric nitrate nonahydrate, 447 g of nickel nitrate hexahydrate, 448 g of cobalt nitrate hexahydrate, 252 g of magnesium nitrate hexahydrate and 4 g of chromium nitrate nonahydrate were dissolved in 1061 g of 16.6 mass % nitric acid solution. 800 g of pure water was also added. The total amount thereof was 4008 g (Bi-containing liquid. Hereinafter referred to as "Liquid B7").

The mass ratio in this case was 4008 (g)/7152 (g)=0.56.

Liquid A7, which was held at 35° C., and Liquid B7, which was held at 35° C., were fed by means of metering pumps to an inlet 1 and an inlet 2, respectively, of a T-shaped stainless steel cylindrical pipe (internal diameter 15 mm, length 300 mm), and the two liquids were merged at an angle whereby the liquids flowed in opposite directions from each other. The thus produced Mo—Bi-containing liquid was fed from the outlet of the T-shaped pipe to a slurry stirring tank. This procedure was carried out for 10 minutes. During this period, the supply ratio was altered within the range 0.5 times to 1.5 times the mass ratio mentioned above (0.56), and all of Liquid A7 and Liquid B7 (100 mass %) were merged.

Specifically, the following procedure was carried out.

Liquid A7 was supplied via a pipe to the T-shaped pipe for 2 minutes at a flow rate of 716 (g/min) while simultaneously supplying Liquid B7 at a flow rate of 401 (g/min) via a pipe. This supply ratio was 401 (g/min)/716 (g/min)=0.56, which was 1.0 times the mass ratio mentioned above (0.56).

Next, the supply flow rates of Liquid A7 and Liquid B7 were altered, and Liquid A7 was supplied at a flow rate of 771 (g/min) for 2 minutes while simultaneously supplying Liquid B7 at a flow rate of 346 (g/min). This supply ratio was 346 (g/min)/771 (g/min)=0.45, which was 0.80 times the mass ratio mentioned above (0.56).

Next, the supply flow rates of Liquid A7 and Liquid B7 were altered, and Liquid A7 was supplied at a flow rate of 607 (g/min) for 2 minutes while simultaneously supplying Liquid B7 at a flow rate of 510 (g/min). This supply ratio was 510 (g/min)/607 (g/min)=0.84, which was 1.5 times the mass ratio mentioned above (0.56).

Next, the supply flow rates of Liquid A7 and Liquid B7 were altered, and Liquid A7 was supplied at a flow rate of 872 (g/min) for 2 minutes while simultaneously supplying Liquid B7 at a flow rate of 244 (g/min). This supply ratio was 244 (g/min)/872 (g/min)=0.28, which was 0.5 times the mass ratio mentioned above (0.56).

Next, the supply flow rates of Liquid A7 and Liquid B7 were altered, and Liquid A7 was supplied at a flow rate of 668 (g/min) for 2 minutes while simultaneously supplying Liquid B7 at a flow rate of 449 (g/min). This supply ratio was 449 (g/min)/668 (g/min)=0.67, which was 1.2 times the mass ratio mentioned above (0.56).

Moreover, the merging temperature for Liquid A7 and Liquid B7 was 35° C. at each stage. The thus produced Mo—Bi-containing liquid was stirred for a further 1 hour at 50° C.

Hereinafter, a catalyst (Catalyst 7) was obtained in the same way as in Working Example 1. This Mo—Bi-containing liquid had a pH of 1 or lower and was in the form of a slurry prior to being spray dried. The standard deviation for Catalyst 7 is shown in Table 1.

[Production of Butadiene Using Catalyst 7 (Fluidized Bed Reaction)]

Butadiene was produced in the same way as in Working Example 1, except that Catalyst 7 was used instead of Catalyst 1. The reaction results are shown in Table 1.

Working Example 8

[Production of Catalyst 8]

A Mo-containing liquid (the same as Liquid A1, but hereinafter referred to as "Liquid A8") and a Bi-containing liquid (the same as Liquid B1, but hereinafter referred to as "Liquid B8") were produced in the same way as in Working Example 1. The mass ratio in this case was 0.36, as in Working Example 1.

The supply ratio of Liquid B8 relative to Liquid A8 was set to fall within the range of 0.5 times to 1.5 times the mass ratio mentioned above (0.36) for an amount corresponding to 60 mass % of the overall supplied amount of the Mo-containing liquid and the Bi-containing liquid. The remaining 40 mass % of the overall supplied amount of the Mo-containing liquid and the Bi-containing liquid was supplied at a supply ratio that fell within a range outside 0.5 times to 1.5 times the mass ratio mentioned above. In other respects, a catalyst (Catalyst 8) was obtained in the same way as in Working Example 1.

Specifically, the following procedure was carried out.

Liquid A8 was supplied via a pipe to the Y-shaped pipe for 2 minutes at a flow rate of 913 (g/min) while simultaneously supplying Liquid B8 at a flow rate of 165 (g/min) via a pipe. This supply ratio was 165 (g/min)/913 (g/min)=0.18, which was 0.5 times the mass ratio mentioned above (0.36).

Next, the supply flow rates of Liquid A8 and Liquid B8 were altered, and Liquid A8 was supplied at a flow rate of 627 (g/min) for 2 minutes while simultaneously supplying Liquid B8 at a flow rate of 451 (g/min). This supply ratio was 451 (g/min)/627 (g/min)=0.72, which was 2.0 times the mass ratio mentioned above (0.36).

Next, the supply flow rates of Liquid A8 and Liquid B8 were altered, and Liquid A8 was supplied at a flow rate of 793 (g/min) for 2 minutes while simultaneously supplying Liquid B8 at a flow rate of 285 (g/min). This supply ratio was 285 (g/min)/793 (g/min)=0.36, which was 1.0 times the mass ratio mentioned above (0.36).

Next, the supply flow rates of Liquid A8 and Liquid B8 were altered, and Liquid A8 was supplied at a flow rate of 973 (g/min) for 2 minutes while simultaneously supplying Liquid B8 at a flow rate of 105 (g/min). This supply ratio was 105 (g/min)/973 (g/min)=0.11, which was 0.3 times the mass ratio mentioned above (0.36).

Next, the supply flow rates of Liquid A8 and Liquid B8 were altered, and Liquid A8 was supplied at a flow rate of 700 (g/min) for 2 minutes while simultaneously supplying Liquid B8 at a flow rate of 378 (g/min). This supply ratio was 378 (g/min)/700 (g/min)=0.54, which was 1.5 times the mass ratio mentioned above (0.36).

Moreover, the merging temperature for Liquid A8 and Liquid B8 was 50° C. at each stage.

Hereinafter, a catalyst (Catalyst 8) was obtained in the same way as in Working Example 1. This Mo—Bi-containing liquid had a pH of 1 or lower and was in the form of a slurry prior to being spray dried.

The standard deviation for Catalyst 8 is shown in Table 1.

[Production of Butadiene Using Catalyst 8 (Fluidized Bed Reaction)]

Butadiene was produced in the same way as in Working Example 1, except that Catalyst 8 was used instead of Catalyst 1. The reaction results are shown in Table 1.

Comparative Example 1

[Production of Catalyst 9]

A Mo-containing liquid (the same as Liquid A1, but hereinafter referred to as "Liquid A9") and a Bi-containing liquid (the same as Liquid B1, but hereinafter referred to as "Liquid B9") were produced in the same way as in Working Example 1.

A Mo—Bi-containing liquid was prepared by introducing Liquid B9, which was held at 50° C., into Liquid A9, which was held at 50° C., while stirring. This introduction was carried out using a quantitative delivery pump.

Specifically, 2845 g of Liquid B9 was supplied at a flow rate of 285 (g/min) to the total amount (7931 g) of Liquid A9. The thus produced Mo—Bi-containing liquid was stirred for a further 1 hour at 50° C. This Mo—Bi-containing liquid had a pH of 1 or lower and was in the form of a slurry prior to being spray dried.

Hereinafter, a catalyst (Catalyst 9) was obtained in the same way as in Working Example 1.

The standard deviation for Catalyst 9 is shown in Table 1.

[Production of Butadiene Using Catalyst 9 (Fluidized Bed Reaction)]

Butadiene was produced in the same way as in Working Example 1, except that Catalyst 9 was used instead of Catalyst 1. Reaction results for butadiene production are shown in Table 1.

Comparative Example 2

[Production of Catalyst 10]

A Mo-containing liquid (the same as Liquid A1, but hereinafter referred to as "Liquid A10") and a Bi-containing liquid (the same as Liquid B1, but hereinafter referred to as "Liquid B10") were produced in the same way as in Working Example 1.

A Mo—Bi-containing liquid was prepared by introducing Liquid A10, which was held at 50° C., into Liquid B10, which was held at 50° C., while stirring. This introduction was carried out using a quantitative delivery pump.

Specifically, 7931 g of Liquid A10 was supplied at a flow rate of 793 (g/min) to the total amount (2845 g) of Liquid B10. The thus produced Mo—Bi-containing liquid was stirred for a further 1 hour at 50° C. This Mo—Bi-containing liquid had a pH of 1 or lower and was in the form of a slurry prior to being spray dried.

Hereinafter, a catalyst (Catalyst 10) was obtained in the same way as in Working Example 1. The standard deviation for Catalyst 10 is shown in Table 1.

[Production of Butadiene Using Catalyst 10 (Fluidized Bed Reaction)]

Butadiene was produced in the same way as in Working Example 1, except that Catalyst 10 was used instead of Catalyst 1. The reaction results are shown in Table 1.

Comparative Example 3

[Production of Catalyst 11]

A Mo-containing liquid (the same as Liquid A1, but hereinafter referred to as "Liquid A11") and a Bi-containing liquid (the same as Liquid B1, but hereinafter referred to as "Liquid B11") were produced in the same way as in Working Example 1.

A Mo—Bi-containing liquid was prepared by introducing Liquid B11, which was held at 50° C., into Liquid A11, which was held at 50° C., while stirring. This introduction was carried out using a quantitative delivery pump.

Specifically, 2845 g of Liquid A1 was supplied at a flow rate of 1138 (g/min) to the total amount (7931 g) of Liquid B11. The thus produced Mo—Bi-containing liquid was stirred for a further 1 hour at 50° C. This Mo—Bi-containing liquid had a pH of 1 or lower and was in the form of a slurry prior to being spray dried.

Hereinafter, a catalyst (Catalyst 11) was obtained in the same way as in Working Example 1. The standard deviation for Catalyst 11 is shown in Table 1.

[Production of Butadiene Using Catalyst 11 (Fluidized Bed Reaction)]

Butadiene was produced in the same way as in Working Example 1, except that Catalyst 11 was used instead of Catalyst 1. The reaction results are shown in Table 1.

Working Example 9

[Production of Catalyst 12]

A Mo-containing liquid (the same as Liquid A1, but hereinafter referred to as "Liquid A12") and a Bi-containing liquid (the same as Liquid B1, but hereinafter referred to as "Liquid B12") were produced at 20 times the masses in Working Example 1 in the same way as in Working Example 1, except that the raw material amounts were 20 times those in Working Example 1.

A Mo—Bi-containing liquid was prepared by introducing Liquid B12, which was held at 50° C., into Liquid A12, which was held at 50° C., while stirring. This introduction was carried out using a quantitative delivery pump.

Specifically, 56.9 kg of Liquid B12 was supplied at a flow rate of 22.8 (kg/min) to the total amount (158.6 kg) of Liquid A12. The thus produced Mo—Bi-containing liquid was stirred for a further 1 hour at 50° C. This Mo—Bi-containing liquid had a pH of 1 or lower and was in the form of a slurry prior to being spray dried. Hereinafter, a catalyst (Catalyst 12) was obtained in the same way as in Working Example 1. The standard deviation for Catalyst 12 is shown in Table 1.

[Production of Butadiene Using Catalyst 12 (Fluidized Bed Reaction)]

Butadiene was produced in the same way as in Working Example 1, except that Catalyst 12 was used instead of Catalyst 1. The reaction results are shown in Table 1.

Comparative Example 4

[Production of Catalyst 13]

A Mo-containing liquid (the same as Liquid A12, but hereinafter referred to as "Liquid A13") and a Bi-containing liquid (the same as Liquid B12, but hereinafter referred to as "Liquid B13") were produced in the same way as in Working Example 9.

A Mo—Bi-containing liquid was prepared by introducing Liquid B13, which was held at 50° C., into Liquid A13, which was held at 50° C., while stirring. This introduction was carried out using a quantitative delivery pump.

Specifically, 56.9 kg of Liquid B13 was supplied at a flow rate of 5.69 (kg/min) to the total amount (158.6 kg) of Liquid A13. The thus produced Mo—Bi-containing liquid was stirred for a further 1 hour at 50° C. This Mo—Bi-containing liquid had a pH of 1 or lower and was in the form of a slurry prior to being spray dried. Hereinafter, a catalyst (Catalyst 13) was obtained in the same way as in Working Example 1. The standard deviation for Catalyst 13 is shown in Table 1.

[Production of Butadiene Using Catalyst 13 (Fluidized Bed Reaction)]

Butadiene was produced in the same way as in Working Example 1, except that Catalyst 13 was used instead of Catalyst 1. The reaction results are shown in Table 1.

TABLE 1

| Catalyst | Liquid A temperature (° C.) | Liquid B temperature (° C.) | pH of Mo—Bi-containing liquid | Supply ratio/mass ratio | Merging angle | Static mixing device | Step (v) | Standard deviation | n-butene conversion rate (%) | Butadiene yield (%) |
|---|---|---|---|---|---|---|---|---|---|---|
| Working Example 1 | 1 | 50 | 50 | <1 | 1.0 | Parallel | Yes | Yes | 0.11 | 99.0 | 90.6 |
| Working Example 2 | 2 | 50 | 50 | <1 | 0.8-1.2 | Parallel | Yes | Yes | 0.15 | 98.8 | 90.2 |
| Working Example 3 | 3 | 50 | 50 | <1 | 0.5-1.5 | Parallel | Yes | Yes | 0.17 | 98.8 | 90.0 |
| Working Example 4 | 4 | 50 | 50 | <1 | 1.0 | Parallel | Yes | Yes | 0.15 | 99.2 | 90.3 |
| Working Example 5 | 5 | 50 | 50 | <1 | 1.0 | Parallel | Yes | No | 0.18 | 98.9 | 90.0 |
| Working Example 6 | 6 | 98 | 98 | <1 | 0.5-1.4 | Perpendicular | No | Yes | 0.20 | 98.0 | 88.5 |
| Working Example 7 | 7 | 35 | 35 | <1 | 0.5-1.5 | Opposing | No | Yes | 0.12 | 99.2 | 89.6 |
| Working Example 8 | 8 | 50 | 50 | <1 | 0.5-1.5 | Parallel | Yes | Yes | 0.20 | 98.5 | 88.2 |
| Comparative Example 1 | 9 | 50 | 50 | <1 | — | — | — | Yes | 0.35 | 96.2 | 83.5 |
| Comparative Example 2 | 10 | 50 | 50 | <1 | — | — | — | Yes | 0.37 | 95.8 | 82.4 |
| Comparative Example 3 | 11 | 50 | 50 | <1 | — | — | — | Yes | 0.32 | 97.7 | 84.2 |
| Working Example 9 | 12 | 50 | 50 | <1 | — | — | — | Yes | 0.18 | 99.0 | 89.8 |
| Comparative Example 4 | 13 | 50 | 50 | <1 | — | — | — | Yes | 0.34 | 98.2 | 84.5 |

Catalysts 1 to 5 and 8 to 13: $Mo_{12}Bi_{0.8}Fe_{2.5}Ni_{4.6}K_{0.12}Rb_{0.05}Mg_{1.1}Ce_{1.5}Si_{45.9}$
Catalyst 6: $Mo_{12}Bi_{1.0}Fe_{1.6}Ni_{2.0}Co_{3.0}Rb_{0.21}Mg_{1.3}Ce_{2.0}Si_{20.4}$
Catalyst 7: $Mo_{12}Bi_{0.4}Fe_{2.3}Ni_{2.5}Co_{2.5}K_{0.06}Rb_{0.08}Mg_{1.6}Ce_{1.2}Cr_{0.02}Si_{29.4}$

INDUSTRIAL APPLICABILITY

The metal oxide catalyst of the present invention can be used in a process for producing a conjugated diolefin from a monoolefin having 4 or more carbon atoms.

In addition, the method and apparatus for producing a metal oxide catalyst of the present invention can be advantageously used to produce a Mo—Bi-containing metal oxide catalyst.

This application is based on a Japanese patent application filed with the Japan Patent Office on 30 May 2016 (Japanese Patent Application No. 2016-107339), and the contents of this earlier application are incorporated by reference in the present application.

What is claimed is:

1. A metal oxide catalyst suitable to produce a conjugated diolefin by an oxidative dehydrogenation reaction between a monoolefin, having 4 or more carbon atoms, and molecular oxygen, the metal oxide catalyst comprising a bulk composition represented by the formula (1):

$$Mo_{12}Bi_pFe_qA_aB_bC_cD_dE_eF_fO_x \qquad (1)$$

wherein A is at least one type of element selected from the group consisting of Ni and Co, B is at least one type of element selected from among alkali metal elements, C is at least one type of element selected from the group consisting of Mg, Ca, Sr, Ba, Zn and Mn, D is at least one type of rare earth element, E is at least one type of element selected from the group consisting of Cr, In and Ga, F is at least one type of element selected from the group consisting of Si, Al, Ti and Zr, O is oxygen, p, q, a, b, c, d, e, f and x denote the number of atoms of Bi, Fe, A, B, C, D, E, F and oxygen, respectively, relative to 12 Mo atoms, and are such that $0.1 \leq p \leq 5$, $0.5 \leq q \leq 8$, $0 \leq a \leq 10$, $0.02 \leq b \leq 2$, $0 \leq c \leq 5$, $0 \leq d \leq 5$, $0 \leq e \leq 5$ and $0 \leq f \leq 200$, and x is the number of oxygen atoms required to satisfy valency requirement of other elements present, wherein a standard deviation of the bulk composition is 0.3 or less, the standard deviation defined by the following formula (2):

$$\text{Standard deviation} = \{((S_1-\mu)^2+(S_2-\mu)^2+\ldots+(S_{100}-\mu)^2)/100[\text{number}]\}^{1/2} \qquad (2)$$

wherein $S_k$ (k is integer of from 1 to 100) is a value obtained by dividing a ratio $(Bi/Mo)_{surf}$ by a ratio $(Bi/Mo)_{bulk}$, wherein the ratio $(Bi/Mo)_{surf}$ is a Bi molar concentration relative to a Mo molar concentration, determined by a SEM-EDX (Scanning Electron Microscopes-Energy Dispersive X-Ray Spectroscopy) compositional analysis, at a surface of the $k^{th}$ catalyst particle among 100 catalyst particles arbitrarily selected, a ratio $(Bi/Mo)_{bulk}$ is the ratio of the Bi molar concentration relative to the Mo molar concentration in the catalyst bulk, as determined by an ICP emission spectroscopic analysis, and μ is an average value of $S_k$ of the 100 catalyst particles arbitrarily selected as defined as $(S_1+S_2 \ldots +S_{100})/100)$.

2. The metal oxide catalyst according to claim 1, wherein the standard deviation is 0.2 or less and p in formula (1) is such that $0.15 \leq p \leq 3$.

3. A method for producing a conjugated diolefin by an oxidative dehydrogenation reaction between a monoolefin, having 4 or more carbon atoms, and molecular oxygen by using the metal oxide catalyst according to claim 1.

4. The method for producing a conjugated diolefin according to claim 3, wherein the monoolefin is n-butene and the conjugated diolefin is 1,3-butadiene.

5. The method for producing a conjugated diolefin according to claim 3, wherein the oxidative dehydrogenation reaction is carried out as a fluidized bed reaction.

6. The metal oxide catalyst according to claim 1, wherein the standard deviation is 0.11 to 0.2.

\* \* \* \* \*